United States Patent [19]

Papageorgiou et al.

[11] Patent Number: 4,560,782
[45] Date of Patent: Dec. 24, 1985

[54] ANTI-TUMOR DIPLATINUM COORDINATION COMPOUNDS

[75] Inventors: Vassilios P. Papageorgiou; Maria Bakola-Christianopoulou; Constantinos A. Tsipis, all of Thessaloniki, Greece

[73] Assignee: Research Corporation, New York, N.Y.

[21] Appl. No.: 548,107

[22] Filed: Nov. 2, 1983

[30] Foreign Application Priority Data

Nov. 19, 1982 [GR] Greece ................................ 71039

[51] Int. Cl.$^4$ ............................................ C07F 15/00
[52] U.S. Cl. .................................... 556/137; 514/492
[58] Field of Search .................................... 260/429 R

[56] References Cited

U.S. PATENT DOCUMENTS

| | | | |
|---|---|---|---|
| 3,892,790 | 7/1975 | Tobe et al. | 260/429 R |
| 3,904,663 | 9/1975 | Tobe et al. | 260/429 R |
| 4,140,707 | 2/1979 | Cleare et al. | 260/429 R |
| 4,200,583 | 4/1980 | Kidani et al. | 260/429 R X |
| 4,283,342 | 8/1981 | Yolles | 260/429 R X |

OTHER PUBLICATIONS

Chemical Abstracts 94 157066q, (1981).
Chemical Abstracts 94 157067r, (1981).

Primary Examiner—Helen M. S. Sneed
Attorney, Agent, or Firm—Scully, Scott, Murphy & Presser

[57] ABSTRACT

Diplatinum complexes of the formulas

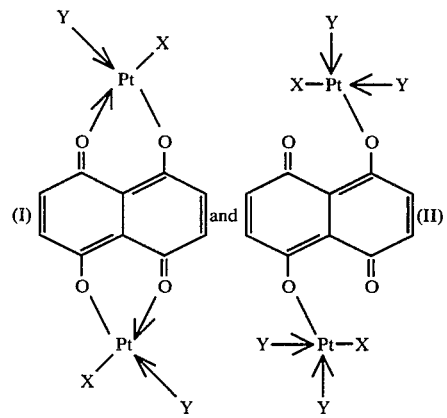

wherein X and Y are ligands, such as Cl and/or $NH_3$, having antineoplastic activity.

8 Claims, 2 Drawing Figures

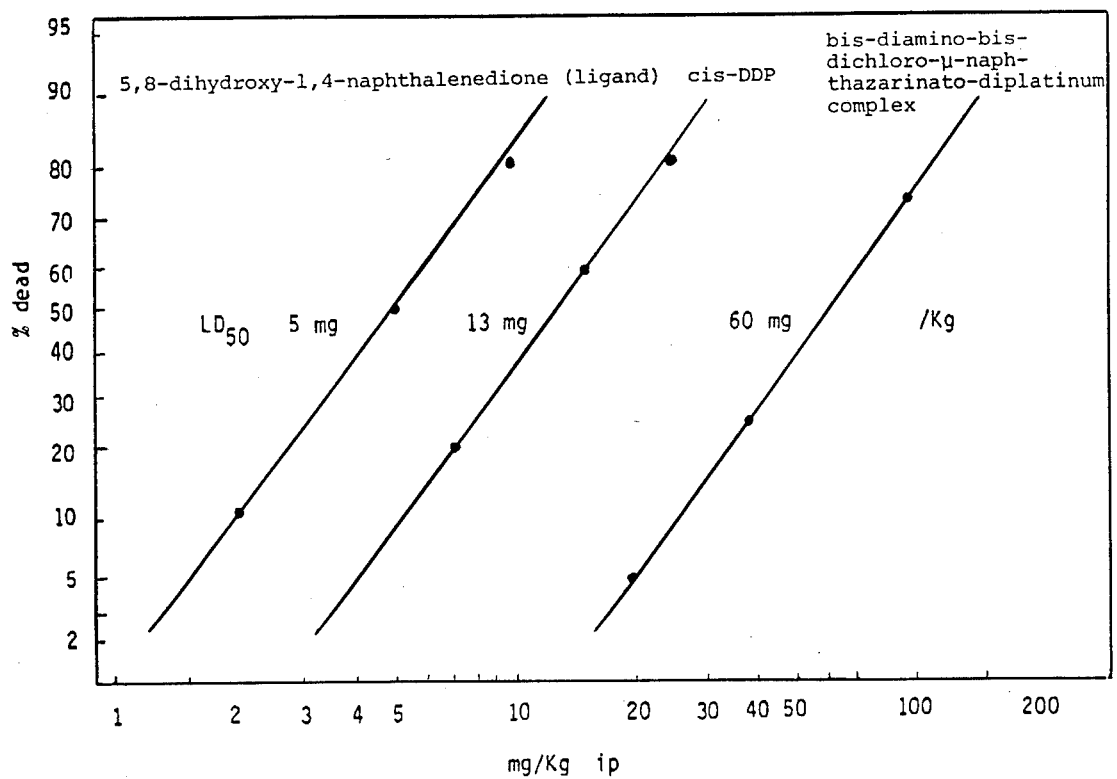
FIG. I  LD curves of bis-diamino-bis-dichloro-μ-naphthazarinato-diplatinum complex, cis-DDP and the ligand. Each curve has been estimated on a group of 20 mice for 10 days.

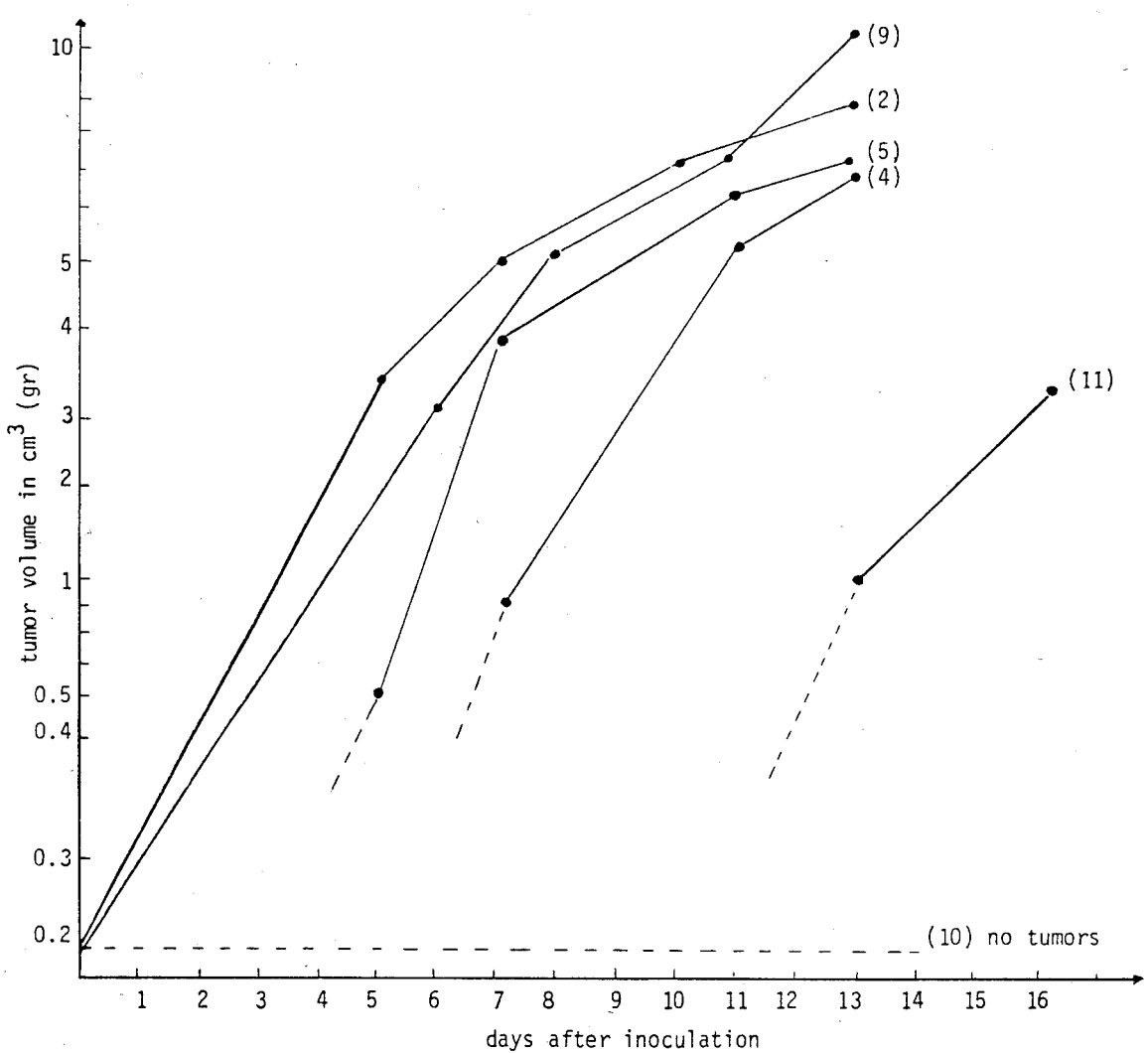
FIG. 2  Growth curves of EAT. In parenthesis the number of the experiment (see table I).
 9 and 2 controls
 5  cis-DDP 6 mg/Kg ip day 1
 4  diplatinum complex 28 mg/Kg ip day 1
 11 cis-DDP 4 mg/Kg ip days 1 and 6
 10 diplatinum complex 20 mg/Kg ip days 1 and 6

ANTI-TUMOR DIPLATINUM COORDINATION COMPOUNDS

BACKGROUND OF THE INVENTION

This invention relates to diplatinum complexes and in particular to diplatinum complexes useful as anti-tumor agents.

The use of transition metal complexes as anti-tumor agents is well documented. While complexes of copper, palladium and iridium have been shown to be effective anti-tumor agents, platinum complexes have recently been receiving most attention.

For example, U.S. Pat. No. 4,177,263 to Rosenberg et al. discloses the effectiveness of cis-dichlorodiammine-platinum (II) ($Pt(II)Cl_2(NH_3)_2$) in the treatment of malignant tumors. U.S. Pat. No. 4,140,707 to Cleare et al. relates to malonato platinum coordination compounds and methods of treating malignant tumors comprising the parenteral administration to an affected animal of a solution of the compound. Further, U.S. Pat. No. 4,200,583 discloses cis-platinum (II) complexes wherein platinum (II) coordinates, 1,2-diamino-cyclohexane (cis-, trans-l or trans-d) are disclosed to exhibit anti-tumor activity.

While platinum complexes, particularly cis-dis-chlorodiammine-platinum (II) (cis-DDP), have been found to be relatively effective for the treatment of a variety of tumors, one disadvantage associated with their use is the high degree of toxicity. Moreover, tumor cells, previously susceptible to certain platinum complexes, such as cis-dichlorodiammine-platinum (cis-DDP), have been discovered which are highly resistant to the compound.

Accordingly, new platinum complexes which eliminate or minimize the disadvantages of the prior art materials are desirable.

SUMMARY OF THE INVENTION

It is, therefore, one object of the present invention to provide novel platinum complexes exhibiting anti-neoplastic activity.

Another object of this invention is to provide novel platinum complexes especially useful as anti-tumor agents.

Still another object of the present invention is to provide platinum complexes, useful as anti-tiumor agents, which are less toxic and/or more potent than prior art platinum complexes.

A further object of this invention is to provide pharmaceutically acceptable compositions containing novel platinum complexes useful as anti-tumor agents.

A still further object of the present invention is to provide a method for the treatment of a host afflicted with a malignant tumor by administering to said host the novel platinum complexes of the present invention.

These and other objects are accomplished herein by providing novel platinum complexes having the general formulas:

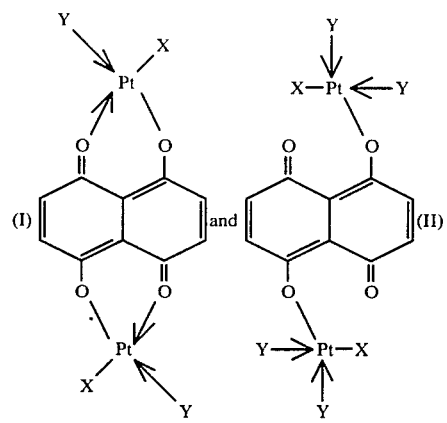

wherein X and Y are monodentate ligands independently selected from the group consisting of Cl, $NH_3$, lower alkyl amines, aryl amines, aralkyl amines, hydroxy lower alkylamines, hydroxylamine, lower alkoxyamines, alkoxyalkylamines, heterocyclic amines, aminoacids, OH, Br, I, $NO_3$, $NO_2$, CN, SCN, monocarboxylates and the like. Moreover, two of the monodentate anionic ligands may be substituted by one bidentate anionic ligand. Suitable bidentate ligands include, for example, $SO_4$, various dicarboxylates, (derived from dicarboxylic acids) such as malonato, oxalato, carbonato, substituted and unsubstituted primary and secondary ethylenediamines, carboxyphthalate and the like. Furthermore, it is to be understood that the substitution of other fused ring ligands in place of the naphthazarinato of the above formula is also contemplated herein. For example, other fused rings include the equivalent anthracene ligands.

Other objects of the present invention are accomplished by providing therapeutic compositions containing the afore-identified active diplatinum compounds of this invention, methods of preparation of these active compounds, and methods for treating tumor afflicted hosts with the novel diplatinum complexes.

BRIEF DESCRIPTION OF THE DRAWINGS

FIG. 1 is a graphical illustration of the LD curves for one of the diplatinum complexes of the present invention, namely bis-diamino-bis-dichloro-$\mu$-naphthazarinato-diplatinum, in comparison with the LD curves for cis-dichlorodiammine-platinum (II) and ligand. Each curve is estimated on a group of 20 mice for 10 days.

FIG. 2 is a graphical illustration of the growth curves of EAT (Erlich Ascites Tumor). The number in the parenthesis corresponds to the number of the experiment recited in Table I, below.

DETAILED DESCRIPTION OF THE INVENTION

In accordance with the present invention, it has been surprisingly found that certain novel diplatinum complexes have extremely potent antineoplastic action. For example, not only are the novel diplatinum complexes of the present invention generally less toxic than prior art monoplatinum complexes, certain of the present compounds are as much as four times more active then even commercial anti-tumor compositions.

In particular, among the diplatinum complexes contemplated by the present invention, two of the more preferred compounds are represented by the formulas:

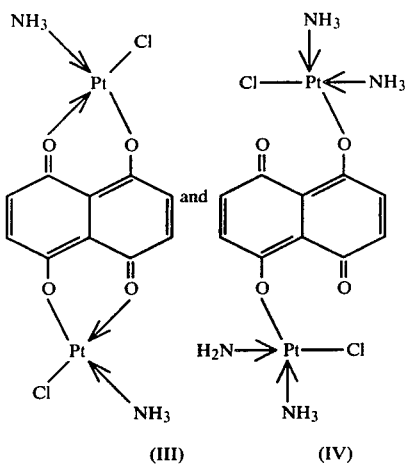

(III)   (IV)

As stated hereinbefore however, diplatinum complexes also contemplated by the present invention include those having the formulas III and IV above wherein other monodentate anionic ligands are substituted for one or more of the NH₃ or Cl substituents. In this regard, suitable other anionic ligands include, for example, OH, Br, I, NO$_3$, NO$_2$, CN, SCN, sulfamate, various carboxylates, lower alkyl amines, (e.g., methyl-, ethyl-, n-propyl-, isopropyl-, n-butyl-amines, etc.), aryl amines, (e.g., aniline), aralkyl amines, (e.g., benzylamine), hydroxy lower alkyl amines (e.g., ethanolamine, propanolamine, etc.), hydroxylamine, lower alkoxy amines (e.g., methoxylamine, etc.), alkoxyalkylamines (e.g., methoxymethylamine, etc.), and heterocyclic amines (e.g., pyridine and aziridine). Also included are the amino acids, i.e., R$_7$—CHNH$_2$—COOH wherein R$_7$ is H, lower alkyl (e.g., methyl, isopropyl, etc.), hydroxy lower alkyl (e.g., hydroxymethyl, hydroxyethyl, etc.), aralkyl (e.g., benzyl, etc.).

It is to be understood that the complex coordination compounds of the invention may include two identical or different monodentate ligands. Moreover, two of the monodentate anionic ligands may be substituted by one bidentate anionic ligand. Suitable bidentate ligands include, for example, SO$_4$, pyrophosphate, dithioxalate, various dicarboxylates (derived from dicarboxylic acids) such as malonato, oxolato, carbonato, carboxyphthalate, and substituted and unsubstituted primary and secondary ethylenediamine. One or both of the carbon atoms of the ethylenediamine may contain substituents such as lower alkyl (e.g., methyl, ethyl), hydroxyl, alkoxy (e.g., methoxy, ethoxy, etc.) and the like. Secondary ethylenediamines wherein one or more of the amine groups contains substituents such as listed above for the carbon atoms of the primary amine and aryl (e.g., phenyl) and aralkyl, (e.g. benzyl) may also be utilized.

Furthermore, it is to be understood that the substitution of other fused ring ligands in place of the naphthazarinato ligands of the above formulas are also contemplated herein. For example, other fused rings include the equivalent anthracene ligands.

The diplatinum complexes shown in structural formulas III and IV above are preferred anti-tumor agents herein while the diplatinum complex of formula III is most preferred. Furthermore, it is also to be understood that both cis and trans forms of the diplatinum complexes illustrated hereinabove are contemplated, with the cis forms being most preferred.

In general, the preparation of platinum coordination compounds is well established in the art. For example, platinum coordination compounds and methods for their production are described by J. C. Bailar, Jr., *The Chemistry of the Coordination Compounds,* Rheinhold Publishing Corp., N.Y. 1956, Chap. 2; Lewis et al., *Modern Coordination Chemistry: Principles and Methods,* Interscience Publishers, Inc. N.Y. 1960 and Kauffman, Inorganic Synthesis, 7, McGraw-Hill Book Co., Inc. N.Y., 1963.

More specifically, the diplatinum complexes of the present invention may be prepared by reacting the appropriate polydentate ligand, such as 5,8-dihydroxy-1,4-naphthalenedione, with a platinum compound, such as K$_2$PtCl$_4$, followed by the addition to the mixture of a suitable compound to provide a further source of ligand (anionic substituent) e.g. selected from the group consisting of NH$_3$, Cl, lower alkyl amine, aryl amine, aralkyl amine, hydroxy lower alkylamine, hydroxylamine, lower alkoxyamine, alkoxyalkylamine, heterocyclic amine, amino acid, OH, Br, I, NO$_2$, NO$_3$, CN, SCN, monocarboxylate and the like. Generally, the reaction is carried out in the presence of organic solvent, such as an alcohol, like methanol or ethanol, and water, said solvents providing appropriate solvent media for the organic and inorganic reactants of the reaction. The reaction may be carried out at atmospheric pressure and room temperature to reflux temperatures for periods ranging from a few hours to a few days, obviously depending upon the specific reactants and reaction conditions employed. The final product is then generally isolated from the reaction mixture using conventional techniques such as filtration and washed with suitable solvents, such as water, ether, alcohol, etc.

Therapeutic, pharmaceutically acceptable compositions containing the active novel-diplatinum complexes of the present invention are also within the scope of this invention. The diplatinum complexes of the therapeutic compositions of the present invention inhibit and induce regression and/or palliation of related neoplasias in mammals when administered in sufficiently effective anti-tumor amounts. Suitable dosages, for example, can be provided in the form of unit dosage compositions which contain the active compound in amounts in the range of from about 10 to about 250 mg/kg/day in mammals. Dosages, however, may range from as little as 1 mg/kg/day up to about 100 mg/kg/day. Of course, the dosage regimen may be adjusted to provide the optimum therapeutic response. For example, several divided doses may be administered daily or the dose may be proportionally reduced as indicated by the exigencies of the therapeutic situation.

A decided practical advantage is that the active compounds of the present invention may be administered in any convenient manner. Typical methods of administration include parenteral, such as intraarterial, intravenous, intramuscular and intraperitoneal. Topical, oral or subcutaneous routes are also contemplated.

The presently preferred method of administration is by injection, i.e. parenteral. Pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be solvent or dispersion medium containing, for example, water, ethanol, polyol (for example, glycerol, propyleneglycol and liquid polyethylene glycol, and the like), suitable mixtures thereof, and vegetable oils, such as corn oil. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding, such as active material for the treatment of disease in living subjects having a diseased condition in which bodily health is impaired as herein disclosed in detail.

The active diplatinum compounds of this invention may also be orally administered, for example, with an inert diluent or with an assimilable edible carrier, or they may be enclosed in hard or soft shell gelatin capsules, or they may be compressed into tablet, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. The amount of active compound in such therapeutically useful compositions is such that a suitable anti-neoplastic, e.g. anti-tumor, dosage will be obtained.

The tablets, troches, pills, capsules, time release capsules and the like may also contain the following: A binder such as gum tragacanth, acacia, corn starch or gelatin; excipients such as dicalcium phospate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As stated previously, in accordance with the present invention the amount of active ingredient administered is that amount which is sufficient to aid regression and/or palliation of the neoplasia or the like in the absence of excessive deleterious side effects of a cytotoxic nature to the host harboring the disease.

As used herein, pharmaceutically acceptable carrier includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is compatable with the active ingredient, its use in the therapeutic compositions is contemplated. Supplementary active ingredients can also be incorporated into the compositions.

Also as used herein, neoplasia or cancer means solid malignancies, such as melanoma, hepatoma, sarcoma, and the like. By the regression and palliation is meant arresting or retarding the growth of the tumor or other manifestation of the disease in the absence of treatment.

The following examples are given by way of illustration in order to assist those of ordinary skill in the art to more readily practice the invention.

EXAMPLE

Preparation of
bis-diamino-bis-dichloro-$\mu$-naphthazarinato-diplatinum
complex, $Pt(\mu$-$C_{10}H_4O_4)(NH_3)_2Cl_2$ 0.19 g (1 mmol) of 5,8-dihydroxy-1,4-naphthalenedione(naphthazarin) were dissolved in 50 ml of ethanol. To the resulting solution, a solution containing 0.83 g (2 mmol) of $K_2PtCl_4$ dissolved in 50 ml of water was added slowly under continuous magnetic stirring, followed by addition of an excess of ammonia solution. The mixture was allowed to stand for 1 day at room temperature under continuous magnetic stirring. During this period a microcrystalline black solid precipitated, which was removed by filtration and washed with water, ethanol and diethyl ether and then dried under vacuum. The isolated compound is soluble in dimethylformamide (DMF) and dimethylsulfoxide (DMSO), and slightly soluble in water and most of the common organic solvents.

---

UV-Vis spectrum:  19.80 kk (log$\epsilon_{mol}$ 3.46)
IR. spectrum:     1610 cm$^{-1}$ vs|v(C—O)$_1$|
              :   1318 cm$^{-1}$ s|v(C—O)$_2$|

455 cm$^{-1}$ w | v(Pt—O)|

Analytical data.
Calcd. for $Pt_2(C_{10}H_4O_4)Cl_2(NH_3)_2$
Found    C = 17.54%, N = 4.09%, H = 1.47%, Pt = 57.10%
         C = 16.34%, N = 4.26%, H = 1.43%, Pt = 56.28%

LD curves are illustrated in FIG. 1. For screening and experimental testing work, doses at about the $LD_{10}$ level were used. The results are summarized in Table I and FIG. 2.

TABLE I

| compound | drug vehicle | tumor | No of exper. | mean survival (c,controls) | TREATMENT route | days | dose mg/kg/ inj. | tumor inhibition | % ILS | survivors | comment |
|---|---|---|---|---|---|---|---|---|---|---|---|
| bis- | corn | EAT | 2 | c | 36 | — | — | — | — | — | 0/10 | — |
| diamino- | oil | | 4 | | 36 | ip | 1 | 28 | yes | 0 | 0/10 | gut toler. |
| bis-di- | | | 8 | c | 30 | — | — | — | — | — | 0/10 | — |
| chloro-μ- | | | 7 | | | ip | 1 | 28 | yes | yes | 7/9 | many cures |
| naphtha- | | | 9 | c | 30 | — | — | — | — | — | 0/10 | — |
| zarinato- | | | 10 | | | ip | 1,6 | 20 | yes | yes | 7/10 | many cures |
| diplati- | | L1210 | 12 | c | 9 | — | — | — | — | — | 0/10 | — |
| num | | | 13 | | 10 | ip | 1 | 20 | yes | 111 | 0/10 | |
| complex | | | 15 | | 12 | ip | 1,6 | 20 | yes | 120 | 0/10 | |
| cis-DDP | saline | EAT | 2 | c | 36 | — | — | — | — | — | 0/10 | — |
| | | | 5 | | 31 | ip | 1 | 6 | yes | 0 | 0/10 | tumor inh. |
| | | | 8 | c | 30 | — | — | — | — | — | 0/10 | |
| | | | 6 | | — | ip | 1 | 6 | yes | 0 | 0/10 | toxic |
| | | | 9 | c | 30 | — | — | — | — | — | 0/10 | — |
| | | | 11 | | — | ip | 1,6 | 4 | yes | yes | 3/10 | some cures |
| | | L1210 | 12 | c | 9 | — | — | — | — | — | 0/10 | |
| | | | 16 | | 12 | ip | 1,6 | 4 | yes | 120 | 0/10 | |
| ligand | corn | EAT | 2 | c | 36 | — | — | — | — | — | 0/10 | — |
| | oil | | 3 | | — | ip | 1 | 2.3 | — | — | 0/10 | toxic | ip = Intraperitoneal
EAT = Erlich Ascites Tumor
ligand = naphthazarin

Obviously, other modifications and variations of the present invention are possible in light of the above teachings. It is therefore to be understood that changes may be made in the particular embodiments of this invention which are within the full intended scope of the invention as defined by the appended claims.

We claim:

1. A diplatinum complex having the general formula:

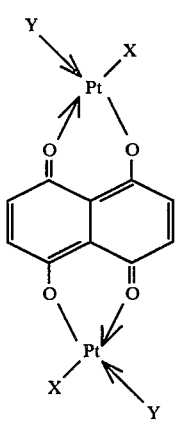

wherein X and Y are monodentate ligands independently selected from the group consisting of $NH_3$, Cl, lower alkyl amines, aryl amines, aralkyl amines, hydroxy lower alkylamines, hydroxylamine, lower alkoxyamines, alkoxyalkylamines, aminoacids, OH, Br, I, $NO_2$, $NO_3$, CN, SCN, monocarboxylates and the like.

2. The diplatinum complex of claim 1 wherein each X is Cl and each Y is $NH_3$.

3. A diplatinum complex having the general formula:

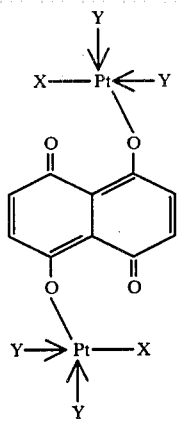

wherein X and Y are monodentate ligands independently selected from the group consisting of Cl, $NH_3$, lower alkyl amines, aryl amines, aralkyl amines, hydroxy lower alkylamines, hydroxylamine, lower alkoxyamines, alkoxyalkylamines, aminoacids, OH, Br, I, $NO_2$, $NO_3$, CN, SCN, monocarboxylates and the like.

4. The diplatinum complex of claim 3 wherein each X is Cl and each Y is $NH_3$.

5. A pharmaceutically acceptable composition in dosage unit form comprising the diplatinum complex of claims 1 or 2 in association with a pharmaceutically acceptable carrier.

6. The pharmaceutical composition of claim 5 wherein said diplatinum complex is provided in an antitumor effective amount.

7. A pharmaceutically acceptable composition in dosage unit form comprising the diplatinum complex of claim 3 or 4 in association with a pharmaceutically acceptable carrier.

8. A diplatinum complex having the formula:
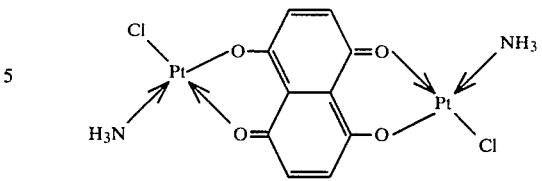
* * * * *